(12) United States Patent
Cai et al.

(10) Patent No.: US 10,980,199 B2
(45) Date of Patent: Apr. 20, 2021

(54) POLYPLOID TWO-LINE HYBRID RICE AND BREEDING METHOD THEREOF

(71) Applicants: WUHAN POLYPLOID BIOTECHNOLOGY CO., LTD, Hubei (CN); HUBEI UNIVERSITY, Hubei (CN)

(72) Inventors: Detian Cai, Hubei (CN); Zhaojian Song, Hubei (CN); Xianhua Zhang, Hubei (CN); Yuhua Liu, Hubei (CN); Yuchi He, Hubei (CN)

(73) Assignees: WUHAN POLYPLOID BIOTECHNOLOGY CO., LTD, Hubei (CN); HUBEI UNIVERSITY, Hubei (CN)

( * ) Notice: Subject to any disclaimer, the term of this patent is extended or adjusted under 35 U.S.C. 154(b) by 0 days.

(21) Appl. No.: 15/927,527

(22) Filed: Mar. 21, 2018

(65) Prior Publication Data

US 2018/0206426 A1 Jul. 26, 2018

Related U.S. Application Data

(63) Continuation of application No. PCT/CN2017/095934, filed on Aug. 4, 2017.

(30) Foreign Application Priority Data

Sep. 29, 2016 (CN) .......................... 201610863449.X

(51) Int. Cl.
| | |
|---|---|
| *A01H 1/04* | (2006.01) |
| *A01H 6/46* | (2018.01) |
| *A01H 1/08* | (2006.01) |
| *C12N 15/82* | (2006.01) |
| *A01H 5/10* | (2018.01) |
| *A01H 1/02* | (2006.01) |

(52) U.S. Cl.
CPC ............... *A01H 1/04* (2013.01); *A01H 1/02* (2013.01); *A01H 1/08* (2013.01); *A01H 5/10* (2013.01); *A01H 6/4636* (2018.05); *C12N 15/8242* (2013.01); *C12N 15/8289* (2013.01)

(58) Field of Classification Search
None
See application file for complete search history.

(56) References Cited

FOREIGN PATENT DOCUMENTS

| CN | 1266615 A | 9/2000 |
|---|---|---|
| CN | 1586134 A | 3/2005 |
| CN | 1951172 A | 4/2007 |
| CN | 104025999 A | 9/2014 |
| CN | 104542258 A | 4/2015 |
| CN | 106386465 A | 2/2017 |
| WO | 2013124844 A1 | 8/2013 |

OTHER PUBLICATIONS

He et al. Planta (2010), vol. 232:1219-1228.*
Cai et al. Sci. China Ser C-life Sci (2007)50(3):356-366.*
Zuo, Bo, "Studies on the Fertility and combination of CMS Lines and Recovery lines of Polyploid Rice", China Excellent Master's Dissertation Database Agricultural Science and Technology, vol. 15.07.2013, A Thesis Submitted for the Degree of Master, Hubei University, pp. 1-67, Wuhan China, Presented: May 20, 2012.
Song, Zhaojian et al., "Studies on the Growth Habits and Characteristics of Two Polyploid Indica-japonica Hybrids with Powerful Heterosis", Scientia Agriculture Sinica, vol. No. 39, Issue No. 1, pp. 1-9, 2006.
Zhang, Yuanyuan, "The research on several male sterile lines and restorer lines of polyploid rice", China Excellent Master's Dissertation Database Agricultural Science and Technology, vol. 15.06. 2017, A Thesis Submitted for the Degree of Master, Hubei University, pp. 1-48, Wuhan China, Presented: May 31, 2016.

* cited by examiner

*Primary Examiner* — Medina A Ibrahim
(74) *Attorney, Agent, or Firm* — Tim Tingkang Xia, Esq.; Locke Lord LLP

(57) ABSTRACT

A method for breeding polyploid two-line hybrid rice includes determining a tetraploid rice photo thermosensitive genic male sterile line with the gene characteristic of PMeS (polyploid meiosis stability) and a tetraploid rice restoring line with the gene characteristic of PMeS; hybridizing and matching by indica sterile/*japonica* restoring or *japonica* sterile/indica restoring hybrid combination; preparing a tetraploid rice hybrid by adopting a tetraploid rice photo thermosensitive genic male sterile line and a tetraploid rice restoring line; and breeding a stable tetraploid rice hybrid combination which is determined as the polyploid two-line hybrid rice combination. The breeding method disclosed by the present invention utilizes the strong heterosis of polyploid rice, and transforms the existing diploid heterosis into the heterosis of polyploid two-line hybrid rice; and by adopting the method disclosed by the present invention, a new polyploid two-line hybrid rice variety with large ears, large grains and high yield can be bred.

2 Claims, 7 Drawing Sheets

HD9802S × HN2026-2X → $F_1$ → $F_1$-4X × HD9802S-4X → $BC_1F_1$ → selecting S strains
(Wuhan) → with rice bunch HN(Hainan) → $BC_1F_2$ × HN164-4X → $RCF_1$ → $F_2$ → → → $F_3$
Doubled
$F_4$ → ... → $F_8$ → PS001-PS010;

FIG. 5A

PA64S × HN2026-2X → $F_1$ → $F_1$-4X × PA64S-4X → $BC_1F_1$ → selecting S strains
(Wuhan) → with rice bunch HN (Hainan) → $BC_1F_2$ × A175-4X → $RCF_1$ → $F_2$ → → → $F_3$
Doubled
$F_4$ → ... → $F_8$ → PS011-PS045;

FIG. 5B

NK58S × Sg99012-2X → $F_1$ → $F_1$-4X × Nongken58S-4X → $BC_1F_1$ → selecting S strains
(Wuhan) → with rice bunch HN (Hainan) → $BC_1F_2$ × HN128-4X → $RCF_1$ → $F_2$ → → → $F_3$
Doubled
$F_4$ → ... → $F_8$ → PS046-PS068.

FIG. 5C

2000 m    Dure-4X ×    Sg99012-4X (japonica, having high setting PMeS gene)
↓
2000          F₁
↓
2001          F₂
↓
2001          F₃
↓⊗
↓
2003          F6  ×   DTS selecting 59 (indica, DTS170/indica and glutinous offspring without threshing)

(japonica, with PMeS gene)   ↓
2003                F₁
↓
2004                F₂ × HN172 (indica)
↓
2004                F₁
↓⊗
2005                F₂
↓⊗
↓⊗
F₁₄   PR001-PR036 (having good comprehensive characters and stable and constant characters)

FIG. 6A

2000    Dure-4X × Sg99012-4X (japonica, having high setting PMeS gene)
2000    F1
2001    F2
2001    F3
2003    F6 × DTS selecting 32 (indica, DTS170/indica and glutinous offspring without threshing)
(japonica, with PMeS gene)
2003    F1
2004    F2 × HN184 (japonica)
2004    F1
2005    F2
F14   PR037- PR060 (having good comprehensive characters and stable and constant characters)
FIG. 6B 2000    Dure-4X ×    HN2026-4X (japonica, having high setting PMeS gene)
2000    F1
2001    F2
2001    F3
2003    F6    ×    DTS selecting 68 (indica, DTS170/indica and glutinous offspring without threshing)
(japonica, with PMeS gene)
2003    F1
2004    F2 × HN054 (indica)
2004    F1
2005    F2
F14    PR061-PR079 (having good comprehensive characters and stable and constant characters)
FIG. 6C

2000   Dure-4X  ×  HN2026-4X (japonica, having high setting PMeS gene)
2000              F1
2001              F2
2001              F3
2003         F6  ×  DTS selecting 15 (indica, DTS170/indica and glutinous offspring without threshing)
(japonica, with PMeS gene)  
2003              F1
2004              F2 × HN269 (japonica)
2004              F1
2005              F2
F14 PR080-PR098 (having good comprehensive characters and stable and constant characters)
FIG. 6D

POLYPLOID TWO-LINE HYBRID RICE AND BREEDING METHOD THEREOF

CROSS-REFERENCE TO RELATED APPLICATIONS

This application is a continuation application of International Patent Application No. PCT/CN2017/095934, filed Aug. 4, 2017, which itself claims priority to Chinese Patent Application No. 201610863449.X, filed Sep. 29, 2016 in the State Intellectual Property Office of P.R. China, which are hereby incorporated herein in their entireties by reference.

FIELD OF THE INVENTION

The present invention relates generally to the field of new crop variety breeding of modern agriculture, and more particularly to polyploid two-line hybrid rice and a breeding method thereof.

BACKGROUND OF THE INVENTION

The background description provided herein is for the purpose of generally presenting the context of the present invention. The subject matter discussed in the background of the invention section should not be assumed to be prior art merely as a result of its mention in the background of the invention section. Similarly, a problem mentioned in the background of the invention section or associated with the subject matter of the background of the invention section should not be assumed to have been previously recognized in the prior art. The subject matter in the background of the invention section merely represents different approaches, which in and of themselves may also be inventions.

Heterosis is a widespread phenomenon of the living nature. Three-line hybrid rice formed by hybridization of three rice lines (a male sterile line, a male sterility maintainer line and a male sterility restoring line) completed by scientists represented by Yuan Longping in 70s of last century is known as the second green revolution, which has a significant promoting role in rice production in China. Hereafter, the Hubei photo thermosensitive genic male sterile line and the two-line restoring line thereof found by Shi Mingsong (1973) promote the rice heterosis utilization to a new level. However, rice planted all over the world currently is diploid, that is, the cells of the rice only contain two sets of chromosomes, namely, $2n=2X=24$. After decades of experiencing the first green revolution of transformation from tall variety to short variety and the second green revolution of transformation from conventional rice variety to hybrid rice variety and obtaining substantial increase of production, rice yield stays in the high-yield gentle hovering period for a long time since the mid-1980s. The increase in production among bred varieties in different generations does not exceed 5% and it is difficult to meet the requirement of 50% increase in 2050 to alleviate the world food crisis. For this reason, Cai Detian, Yuan Longpin, et al. (2001) proposed a new strategy of 'breeding super rice by utilizing distant hybridization and polyploid dual advantages' from the view of evolutionary biology. After research of 20 years, they determined a three-step strategy of polyploid rice inter-sub specific, inter-specific and inter-genome heterosis utilization, and solved the bottleneck problem of low setting percentage of polyploid rice breeding as the priority. They invented a patented technology of efficiently inducing to form the polyploid rice by utilizing combination of tissue culture and colchicines treatment and bred a high setting variety line with PMeS (Polyploid meiosis stability), breaking the bottleneck problem of low setting percentage of the polyploid rice, thus causing the rapid development of breeding of the polyploid rice. A large quantity of polyploid rice materials have been formed, and a batch of conventional polyploidy rice line enters a variety regional trail stage. Making full use of the polyploid heterosis, breeding the polyploid rice sterile line and the polyploid rice restoring line and preparing the polyploid hybrid push rice production to a new stage, thus playing a significant role in guaranteeing world food safety. If it is evolved from the diploid wild species to the cultivated tetraploid or hexaploid species like wheat, cotton and rape, and the yield has a fold increase, the bred polyploidy rice with four sets or six sets of chromosomes has a potential of yield increase of 50%, which can fundamentally relive the world food crisis.

Therefore, a heretofore unaddressed need exists in the art to address the aforementioned deficiencies and inadequacies.

SUMMARY OF THE INVENTION

According to the present invention, the strong heterosis of sturdy stalks, enlarged floral organs, large ears and large grains, large pollen quantity, large pollen grains, high setting percentage and the like of polyploids is utilized, and combined with the existing diploid heterosis to realize the polyploid two-line hybrid rice heterosis, and thus, a new rice breeding path is developed. The polyploid rice two-line sterile line and restoring line are researched to perform hybridizing and matching, so as to form a tetraploid sterile line, restoring line and hybrid rice line with cells containing chromosome, $4X=48$. The present invention not only can overcome the incompatibility of indica and *japonica* subspecies hybridization, but also has greater yield increasing potential and resistance advantages in comparison with distant hybridization and polyploid dual advantages, and thus having significant meaning for solving world food crisis.

An objective of the present invention is to provide a breeding method for polyploid two-line hybrid rice, and realizes polyploid two-line hybrid rice heterosis by utilizing the strong heterosis of sturdy stalks, enlarged floral organs, large ears and large grains, large pollen quantity, large pollen grains, high setting percentage and the like of polyploids, and combining with the existing diploid heterosis.

Another objective of the present invention is to provide tetrapoid two-line hybrid rice, which is the tetraploid two-line hybrid rice obtained by adopting a tetraploid rice photo thermosensitive genic male sterile line with the gene characteristic of PMeS and a tetraploid rice restoring line with the gene characteristic of PMeS through the abovementioned breeding method.

In order to realize the aims of the present invention, the following technical scheme is adopted:

A breeding method for polyploid two-line hybrid rice, characterized by comprising the following steps:

(a) determining a tetraploid rice photo thermosensitive genic male sterile line with the gene characteristic of PMeS and a tetraploid rice two-line restoring line with the gene characteristic of PMeS;

(b) hybridizing and matching the indica sterile line and the *japonica* restoring line or the *japonica* sterile line and the indica restoring line according to a hybrid combination manner of indica sterile/*japonica* restoring or *japonica* sterile/indica restoring;

(c) performing heterosis detection analysis on the tetraploid rice photo thermosensitive genic male sterile line in step a in the aspects of growth period, morphological character, flowering habit, sterile and transformation characteristics, heterogamety and preparation combination;

(d) performing heterosis detection analysis on the tetraploid rice two-line restoring line in step a in the aspects of growth period, morphological characteristics, flowering habit, anther characteristics, heterogamety and preparation combination;

(e) selecting different tetraploid rice photo thermosensitive genic male sterile lines and tetraploid rice two-line restoring lines to prepare tetraploid rice hybrids of different combinations;

(f) performing line comparison on the tetraploid rice hybrids of different combinations prepared in step e, and comparing with the tetraploid rice two-line restoring lines and control diploid hybrid rice from the aspects of growth period, morphological characteristics, setting percentage, resistance and flowering habit; and (g) selecting stable tetraploid rice hybrids with excellent morphological characteristics, proper growth period, relatively strong resistance, setting percentage of over 80% and yield increase of more than 3% than the tetraploid rice two-line restoring lines and the control diploid hybrid rice, and determining as a tetraploid two-line hybrid rice combination.

In the scheme, the tetraploid rice photo thermosensitive genic male sterile line with the gene characteristic of PMeS is selected from the following 68 lines: PS001, PS002, PS003, PS004, PS005, PS006, PS007, PS008, PS009, PS010, PS011, PS012, PS013, PS014, PS015, PS016, PS017, PS018, PS019, PS020, PS021, PS022, PS023, PS024, PS025, PS026, PS027, PS028, PS029, PS030, PS031, PS032, PS033, PS034, PS035, PS036, PS037, PS038, PS039, PS040, PS041, PS042, PS043, PS044, PS045, PS046, PS047, PS048, PS049, PS050, PS051, PS052, PS053, PS054, PS055, PS056, PS057, PS058, PS059, PS060, PS061, PS062, PS063, PS064, PS065, PS066, PS067, PS068. More preferably, the tetraploid rice photo thermosensitive genic male sterile line with the gene characteristic of PMeS is selected from the following three lines: PS001, PS002, PS003.

In the scheme, the tetraploid rice two-line restoring line with the gene characteristic of PMeS is selected from the following 98 lines: PR001, PR002, PR003, PR004, PR005, PR006, PR007, PR008, PR009, PR010, PR011, PR012, PR013, PR014, PR015, PR016, PR017, PR018, PR019, PR020, PR021, PR022, PR023, PR024, PR025, PR026, PR027, PR028, PR029, PR030, PR031, PR032, PR033, PR034, PR035, PR036, PR037, PR038, PR039, PR040, PR041, PR042, PR043, PR044, PR045, PR046, PR047, PR048, PR049, PR050, PR051, PR052, PR053, PR054, PR055, PR056, PR057, PR058, PR059, PR060, PR061, PR062, PR063, PR064, PR065, PR066, PR067, PR068, PR069, PR070, PR071, PR072, PR073, PR074, PR075, PR076, PR077, PR078, PR079, PR080, PR081, PR082, PR083, PR084, PR085, PR086, PR087, PR088, PR089, PR090, PR091, PR092, PR093, PR094, PR095, PR096, PR097, PR098. More preferably, the tetraploid rice two-line restoring line with the gene characteristic of PMeS is selected from the following three lines: PR005, PR027, PR076.

In the scheme, the control diploid hybrid in step g is Fengliangyou No. 4.

Tetraploid two-line hybrid rice, 2n=4X=48, obtained by breeding with the breeding method of the polyploid two-line hybrid rice, has the characteristics of good growth vigour, more tillers, long rice ears, more ear grains, relatively strong resistance and setting percentages of more than 80%, and is named as PHXXX, wherein XXX is a three-digit number.

According to the present invention, the family tree of the tetraploid rice photo thermosensitive genic male sterile line (PS001-PS068) with the gene characteristic of PMeS is as follows:

(1) The PS001-PS010 family tree is shown in FIG. 5A.
(2) The PS011-PS045 family tree is shown in FIG. 5B.
(3) The PS046-PS068 family tree is shown in FIG. 5A.

The breeding procedures will be illustrated by taking PS006 as an example: a. determining HD9802S with photo thermosensitive genic male sterility and rice strain HN2026-2X with polyploid meiosis stability (PMeS) as parents; b. hybridizing a diploid photo thermosensitive genic male sterile line with a diploid PMeS line, that is, hybridizing the diploid sterile line HD9802S with HN2026-2X; c. cultivating and doubling $F_1$ hybrid plant young ears to form a hybrid tetraploid, that is, performing tissue culture by adopting young ears of a hybrid plant hybridized by HD9802S× HN2026-2X in the period from the secondary branch differentiation phase of ear differentiation to the meiosis phase so as to form callus in vigorous growth, and then transferring the callus into a doubled culture solution for cultivation and then differentiating into a tetraploid hybrid $F_1$-4X; d. backcrossing the $F_1$-4X with the tetraploid photo thermosensitive genic male sterile line HD9802S-4X, that is, castrating the abovementioned hybrid plant obtained in a doubled way while blooming and backcrossing with the tetraploid HD9802S-4X (HD9802S-4X is formed by cultivating and doubling HD9802S plant young ears) of the photo thermosensitive genic male sterile line so as to obtain a first backcross generation of hybrid $BC_1F_1$; e. selecting the tetraploid genic male sterile strain (S strain, Wuhan) from the backcross descendants; f. in order to determine the fertility of the selected tetraploid genic male sterile strain in the fertile period with low temperature and short daylength, transferring the rice bunch of the sterile strain determined in summer to Hainan, to recover the fertility in the state with low temperature and short daylength and achieve selfing setting, and thus obtaining $BC_1F_2$; g. performing composite hybridization on $BC_1F_2$ and another tetraploid rice line HN164-4X (the derivative offspring of Sg99012) with PMeS genes to obtain $RCF_1$, enabling $RCF_1$ to perform selfing to obtain $RCF_2$ ($F_2$ for short); h. selecting an S strain therefrom for selfing to form $F_3$, enabling a male sterile strain to perform selfing to obtain $F_4$, in the same way, selfing is continuously performed by 6 generations to obtain $F_8$, that is, the sterile strain is selected in Wuhan, and then the rice bunch is carried to Hainan for seed reproduction and selfing by 6 generations to obtain $F_8$, i. detecting the stability of the $F_8$-generation tetraploid photo thermosensitive genic male sterile line, including the chromosome number (4X=48), the sterile morphological characteristics of anther, the fertility of pollen, the stigma traits, fertility transformation in light and temperature conditions, and heterogamety and heterosis of hybridization with the tetraploid restoring line; j. determining the stable and constant tetraploid rice sterile line as the polyploid photo thermosensitive genic male sterile line, and after multiple items of detection and comparison of step i, determining the bred male sterile line with stable and constant morphological characteristics, stable sterility (percentage of sterility being 100%, sterility degree being 99.5%), high setting percentage (greater than 40%) in the fertile period, good heterogamety and strong matched heterosis as the tetraploid photo thermosensitive genic male sterile line, named as PS006; and the tetraploid rice PS006 has the morphological characteristics of sturdy stalks and dark green leave color and are uniform.

The breeding procedures will be illustrated by taking PS012 as an example: a. determining PA64S with photo thermosensitive genic male sterility and rice strain HN2026-2X with polyploid meiosis stability (PMeS) as parents; b. hybridizing a diploid photo thermosensitive genic male sterile line with a diploid PMeS line, that is, hybridizing the diploid sterile line PA64S with HN2026-2X; c. cultivating and doubling $F_1$ hybrid plant young ears to form a hybrid tetraploid $F_1$-4X, that is, performing tissue culture by adopting young ears of a hybrid plant hybridized by PA64S× HN2026-2X in the period from the secondary branch differentiation phase of ear differentiation to the meiosis phase so as to form callus in vigorous growth, and then transferring the callus into a doubled culture solution for cultivation and then differentiating into a tetraploid hybrid $F_1$-4X; d. backcrossing the tetraploid hybrid $F_1$-4X with the tetraploid of the photo thermosensitive genic male sterile line, that is, castrating the abovementioned hybrid plant obtained in a doubled way while blooming and backcrossing with the tetraploid PA64S-4X (PA64S-4X is formed by cultivating and doubling PA64S plant young ears) of the photo thermosensitive. genic male sterile line so as to obtain a first backcross generation of hybrid $BC_1F_1$; e. selecting the tetraploid genic male sterile strain (S strain, Wuhan) from the backcross descendants; f. in order to determine the fertility of the selected tetraploid genic male sterile strain in the fertile period with low temperature and short daylength, transferring the rice bunch of the sterile strain determined in summer to Hainan, to recover the fertility in the state with low temperature and short daylength and achieve selfing setting, and thug obtaining $BC_1F_2$; g. performing composite hybridization on the $BC_1F_2$ and another tetraploid rice line A175-4X (the derivative offspring of HN2026) with PMeS genes to obtain $RCF_1$, enabling $RCF_1$ to perform selfing to obtain $RCF_2$ ($F_2$ for short); h. selecting an S strain therefrom for selfing to form $F_3$, enabling a male sterile strain to perform selfing to obtain $F_4$, in the same way, selfing is continuously performed by 6 generations to obtain $F_8$, that is, the sterile strain is selected in Wuhan, and then the rice bunch is carried to Hainan for seed reproduction and selfing by 6 generations to obtain $F_8$; i. detecting the stability of the $F_8$-generation tetraploid photo thermosensitive genic male sterile line, including the chromosome number (4X=48), the sterile morphological characteristics of anther, the fertility of pollen, the stigma traits, the fertility transformation in light and temperature conditions, and heterogamety and heterosis of hybridization with the tetraploid restoring line; j. determining the stable and constant tetraploid rice sterile strain as the polyploid photo thermosensitive genic male sterile line, and after multiple items of detection and comparison of step i, determining the bred male sterile line with stable and constant morphological characteristics, stable sterility (percentage of sterility being 100%, sterility degree being 99.5%), high setting percentage (greater than 40%) in the fertile period, good heterogamety and strong matched heterosis as the tetraploid photo thermosensitive genic male sterile line, PS012 for short.

The family tree of the tetraploid two-line restoring line (PR001-PR098) with the gene characteristic of PMeS is as follows:

(1) The PR001-PR036 family tree is shown in FIG. 6A.
(2) The PR037-PR060 family tree is shown in FIG. 6B.
(3) The PR061-PR079 family tree is shown in FIG. 6C.
(4) The PR061-PR079 family tree is shown in FIG. 6D.

The breeding procedures will be illustrated by taking PR003 as an example: a. on the basis of clarifying the characteristics of a two-line photo thermosensitive restoring line and the key function of PMeS gene parents in breeding of polyploidy rice, determining the tetraploid rice line Dure (japonicaclinous type) and the rice line Sg99012 with the gene characteristic of PMeS as the primary hybrid parents of a breeding restoring line; b. hybridizing by taking the tetraploid japonicaclinous rice line Dure as the female parent and the tetraploid rice line Sg99012 with PMeS genes as the male parent, and after continuous selfing of 6 generations of the hybrid offspring, performing composite hybridization by taking the tetraploid indica rice line-DTS selecting 59 (DTS170/indica and glutinous rice without threshing) as the male parent; c. according to an ideal plant type mode of the polyploid rice and the characteristics of large ears and large grains of the polyploidy rice, specifically selecting a single plant meeting the breeding objective, and after selfing of a composite hybrid of one generation, performing composite hybridization on the fine tetraploid rice line HN172 with PMeS genes, and performing molecular marker detection and screening on the composite hybridization offspring by utilizing molecular markers related to high fecundity, disease resistance, insect resistance, drought resistance and quality characters of the rice; d. comparing different strains of each generation by further performing selfing and selecting of multiple generations, selecting a more excellent single plant, and performing continuous selfing for multiple generations until the strain characters are basically stable; e. comparing different reselected strains, performing molecular marker detection and screening again by utilizing molecular markers related to high fecundity, disease resistance, insect resistance, drought resistance and quality characters of the rice, and selecting and determining a stable strain with good high yield property, excellent ear and grain characters and relatively strong resistance and having detection molecular markers as a preferable strain; f. performing test crossing with the polyploidy rice photo thermosensitive genic male sterile lines of different types by taking the preferable strain as the male parent; and g. performing flora comparison on different test crossing matched hybrids, and selecting the hybrid combination and the restoring line thereof with excellent form, relatively strong resistance, strong combining ability and strong heterosis through morphological characteristics, combining ability and heterosis detection, wherein the restoring line is the tetraploid rice two-line restoring line, named as PR003.

Rice strains related in the breeding method disclosed by the present invention are all existing opened rice strains, and the detailed information is as follows:

Pei' ai 64S (PA64S): Pei' ai 64S is an indica rice low thermosensitive male sterile line which is bred by hybridizing by taking Nongken 58S as the female parent and Pei' ai 64 as the male parent, selecting a genic male sterile strain similar to Pei' ai 64 at $F_2$ to be backcrossed with Pei' ai 64, and performing multi-generation bidirectional selection on the hybrid offspring in Changsha and Hainan.

Nongken 58S (NK58S): Nongken 58S is a *japonica* photosensitive genic male sterile line bred from *japonica* variety Nongken 58 by Chinese scientist, Shi Mingsong, in 1973.

Huda 9802S (HD9802S): Huda 9802S is a rice early indica type thermosensitive genic male sterile line bred by multi-generation breeding and low temperature screening by taking Huda51 as the female parent and Hongfuzao as the male parent for hybridization by Academy of Life Science of Hubei University.

PMeS-1-(Sg99012): PMeS-1 (Sg99012) is a polyploid rice line PMeS-1 bred from the crossed polyploid offspring of indica and *japonica* through several years of hybridization of indica and *japonica* and backcrossing selection and detection by the polyploid rice lab of Academy of Life Science of Hubei University and having polyploid meiosis stability (PMeS). It has already been published in a journal literature 'Cai Detian, Chen Jianguo, Chen Dongling, et al. Breeding of Two Polyploid Rice Lines Having Polyploid Meiosis Stability. SCIENCE CHINA, 2007, 37 (2):217-226'.

PMeS-2 (HN2026): PMeS-2 (HN2026) is a tetraploid rice line PMeS-2 bred from the crossed polyploid offspring of indica and *japonica* by the polyploid rice lab of Academy of Life Science of Hubei University and having polyploid meiosis stability (PMeS). It has already been published in a journal literature 'Cai Detian, Chen Jianguo, Chen Dongling, et al. Breeding of Two Polyploid Rice Strains Having Polyploid Meiosis Stability. SCIENCE CHINA, 2007, 37 (2):217-226'.

HN164-4X: HN164-4X is a derivative offspring polyploid rice line HN164-4X bred by taking the polyploid rice line PMeS-1 (Sg99012) having polyploid meiosis stability as the parent by the polyploid rice lab of Academy of Life Science of Hubei University and having the characteristic of meiosis stability and excellent agronomic characters.

HN128-4X: HN128-4X is a derivative offspring polyploid rice line HN164-4X bred by taking the polyploid rice strain PMeS-1 (Sg99012) having polyploid meiosis stability as the parent by the polyploid rice lab of Academy of Life Science of Hubei University and having the characteristic of meiosis stability and excellent agronomic characters.

A175-4X: A175-4X is a derivative offspring polyploid rice line A175-4X bred by taking the polyploid rice line PMeS-2 (HN2026) having polyploid meiosis stability as the parent by the polyploid rice lab of Academy of Life Science of Hubei University and having the characteristic of meiosis stability and excellent agronomic characters.

Tetraploid *japonica* rice line Dure: the tetraploid *japonica* rice line Dure is tetraploid *japonica* rice formed by doubling the filial generation of wide compatible rice variety Dular and C27 (a gift from the researcher, Yang Zhenyu, of Shenyang Academy of Agricultural Science) by the research group.

DTS170: DTS170 is the tetraploid indica rice obtained by performing chromosome doubling and breeding on the hybrid offspring of 'Laser No. 4' rice variety by Academy of Life Science of Hubei University.

DTS selecting 59, DTS selecting 32, DTS selecting 68, DTS selecting 15: they are the polyploidy rice lines bred from the filial generation of DTS170 and 'indica and glutinous-4X without threshing'.

HN172, HN184, HN054, HN269: they are derivative offspring polyploid rice lines bred by taking the polyploid rice line PMeS-1 (Sg99012) having polyploid meiosis stability as the parent by Academy of Life Science of Hubei University and having the characteristic of meiosis stability and excellent agronomic characters.

HN362: HN362 is a derivative offspring polyploid rice line bred by taking the polyploid rice line PMeS-2 (HN2026) having polyploid meiosis stability as the parent by Academy of Life Science of Hubei University and having the characteristic of meiosis stability and excellent agronomic characters.

Beneficial effects of the invention: the breeding method disclosed by the present invention transforms the existing diploid heterosis into the polyploidy two-line hybrid rice heterosis by utilizing the strong heterosis of the polyploid rice, the polyploid sterile line and restoring line bred by solving the bottleneck problem of low setting percentage of the polyploidy rice by using the PMeS gene line, so as to breed the new variety of polyploidy two-line hybrid rice with large ears, large grains and high yield.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIGS. 5A-5C show a PS001-PS010 family tree, a PS011-PS045 family tree, and a PS046-PS068 family tree, respectively.

FIGS. 6A-6D show a PR001-PR036 family tree, a PR037-PR060 family tree, a PR061-PR079 family tree, and a PR061-PR079 family tree, respectively.

DETAILED DESCRIPTION OF THE INVENTION

Figure 1:
FIG. 1 is the picture of real products of the tetraploid two-line hybrid rice PH015 and parents thereof of embodiment 1, wherein the left is PS001 tetraploid rice two-line sterile line (female parent); the middle is the tetraploid two-line hybrid rice PH015; and the right is PR005 tetraploid rice two-line restoring line (male parent).

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more". The word "exemplary" is used herein to mean "serving as an example, instance, or illustration". Any aspect described herein as "exemplary" is not necessarily to be construed as preferred or advantageous over other aspects. Unless specifically stated otherwise, the term "some" refers to one or more. Combinations such as "at least one of A, B, or C", "one or more of A, B, or C", "at least one of A, B, and C", "one or more of A, B, and C", and "A, B, C, or any combination thereof" include any combination of A, B, and/or C, and may include multiples of A, multiples of B, or multiples of C. Specifically, combinations such as "at least one of A, B, or C", "one or more of A, B, or C", "at least one of A, B, and C", "one or more of A, B, and C", and "A, B, C, or any combination thereof" may be A only, B only, C only, A and B, A and C, B and C, or A and B and C, where any such combinations may contain one or more member or members of A, B, or C. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. The words "module", "mechanism", "element", "device" and the like may not be a substitute for the word "means". As such, no claim element is to be construed as a means plus function unless the element is expressly recited using the phrase "means for". It should also be understood that one or more steps within a method may be executed in different order (or concurrently) without altering the principles of the invention.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more thin one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" to another feature may have portions that overlap or underlie the adjacent feature.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below can be termed a second element, component, region, layer or section without departing from the teachings of the disclosure.

Furthermore, relative terms, such as "lower" or "bottom" and "upper" or "top", may be used herein to describe one element's relationship to another element as illustrated in the figures. It will be understood that relative terms are intended to encompass different orientations of the device in addition to the orientation shown in the figures. For example, if the device in one of the figures is turned over, elements described as being on the "lower" side of other elements would then be oriented on the "upper" sides of the other elements. The exemplary term "lower" can, therefore, encompass both an orientation of lower and upper, depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

Typically, terms such as "about," "approximately," "generally," "substantially," and the like unless otherwise indicated mean within 20 percent, preferably within 10 percent, preferably within 5 percent, and even more preferably within 3 percent of a given value or range. Numerical quantities given herein are approximate, meaning that the term "about," "approximately," "generally," or "substantially" can be inferred if not expressly stated.

The description is now made as to the embodiments of the invention in conjunction with the accompanying drawings. It should be understood that specific embodiments described herein are merely intended to explain the invention, but not intended to limit the invention. Various modifications to these aspects will be readily apparent to those skilled in the art, and the generic principles defined herein may be applied to other aspects.

Embodiment 1 the Breeding Process of the Tetraploid Two-Line Hybrid Rice PH015

(a) Determining a tetraploid rice photo (thermo) sensitive genic male sterile line with the gene characteristic of PMeS and a tetraploid rice two-line restoring line with the gene characteristic of PMeS; and adopting the tetraploid rice genic male sterile line PS001 containing PMeS genes as the sterile line for preparing a two-line tetraploid hybrid combination and the tetraploid rice two-line restoring line PR005 containing PMeS genes as the restoring line of the tetraploid two-line hybrid rice;

(b) determining that the hybrid combination manner of indica sterile/*japonica* restoring is used for hybridizing and matching the indica sterile line PS001 and the *japonica* restoring line PR005;

(c) performing heterosis detection on the PS001 tetraploid rice two-line sterile line in the aspects of growth period, morphological characters, flowering habit, sterile and transformation characteristics, heterogamety and preparation combination;

(d) performing heterosis detection analysis on the PR005 tetraploid two-line restoring line in the aspects of growth period, morphological characteristics, flowering habit, anther characteristics, heterogamety and preparation combination;

(e) preparing tetraploid rice hybrids by adopting the PS001 tetraploid rice two-line sterile line and the PR005 tetraploid two-line restoring line;

(f) performing line comparison on the prepared tetraploid rice hybrids, and comparing with the tetraploid rice two-line restoring line and control diploid hybrid from the aspects of growth period, morphological characteristics, resistance and flowering habit and setting percentage;

(g) breeding the combination hybrid of PS001×PR005, which is specifically shown as a uniform stable tetraploid rice hybrid with excellent morphological characteristics, appropriate growth period (sown in appropriate reason in Wuhan, with the total growth period of 135-138 days), relatively strong resistance, setting percentages of more than 80%, and yield increase of more than 5.2% than the tetraploid rice restoring lines and the control diploid hybrid, and determining as the tetraploid two-line hybrid rice, named as PH015.

As shown in FIG. 1, FIG. 1 is the picture of real products of the tetraploid two-line hybrid rice PH015 and parents thereof of the present embodiment, wherein the left is PS001 tetraploid rice two-line sterile line (female parent); the middle is the tetraploid two-line hybrid rice PH015; and the right is PR005 tetraploid rice two-line restoring line (male parent). It can be seen from the drawing: compared with the parents, hybrid PH015 shows better growth vigour and tillering ability and has longer rice ears and more ear grains, indicating that the tetraploid two-line hubrid rice has strong heterosis.

Figure 4:
FIG. 4 is the picture of the seed production field of the tetraploid two-line hybrid rice, wherein the relatively short plants in the middle are the PS001 tetraploid rice photo thermosensitive genic male sterile line (female parent); and the relatively high plants in two sides are the PR005 tetraploid rice two-line restoring line (male parent).

As shown in FIG. 4, FIG. 4 is the picture of real products of field seed production of the tetraploid two-line hybrid rice PH015 of the present embodiment, wherein the relatively short plants in the middle are the PS001: tetraploid rice photo thermosensitive genic male sterile line (female parent); and the relatively high plants in two sides are the PR005: tetraploid rice two-line restoring line (male parent). It can be seen from the drawing: the flowering phase of the parents can meet each other, and natural outcrossing setting is good, indicating that the tetraploid two-line hybrid rice can well realize large field seed production, and a large quantity of hybrids can be harvested, thus being beneficial to large-area production and application.

Embodiment 2 the Breeding Process of the Tetraploid Two-Line Hybrid Rice PH083

(a) Determining a tetraploid rice photo (thermo) sensitive genic male sterile line with the gene characteristic of PMeS and a tetraploid rice two-line restoring line with the gene characteristic of PMeS; and adopting the tetraploid rice genic male sterile line PS002 containing PMeS genes as the sterile line for preparing a two-line tetraploid hybrid combination and the tetraploid rice two-line restoring line PR027 containing PMeS genes as the restoring line of the tetraploid two-line hybrid rice;

(b) determining that the hybrid combination manner of indica sterile/*japonica* restoring is used for hybridizing and matching the indica sterile line PS002 and the *japonica* restoring line PR027;

(c) performing heterosis detection on the PS002 tetraploid rice two-line sterile line in the aspects of growth period, morphological characters, flowering habit, sterile and transformation characteristics, heterogamety and preparation combination;

(d) performing heterosis detection analysis on the PR027 tetraploid two-line restoring line in the aspects of growth period, morphological characteristics, flowering habit, anther characteristics, heterogamety and preparation combination;

(e) preparing tetraploid rice hybrids by adopting the PS002 tetraploid rice two-line sterile line and the PR027 tetraploid two-line restoring line;

(f) performing line comparison on the prepared tetraploid rice hybrids, and comparing with the tetraploid rice restoring line and control diploid hybrid from the aspects of growth period, morphological characteristics, resistance and flowering habit and setting percentage;

(g) breeding the combination hybrid of PS002×PR027, which is specifically shown as a uniform stable tetraploid combination hybrid with excellent morphological characteristics, appropriate growth period (sown in appropriate reason in Wuhan, with the total growth period of 133-136 days), relatively strong resistance, setting percentages of more than 86%, and yield increase of more than 6.8% than the tetraploid rice restoring lines and the control diploid hybrid, and determining as the tetraploid two-line hybrid rice, named as PH083.

Figure 2:
FIG. 2 is the picture of real products of the tetraploid two-line hybrid rice PH083 and parents thereof of embodiment 2, wherein the left is the PS002 tetraploid rice two-line sterile line (female parent); the middle is the tetraploid two-line hybrid rice PH083; and the right is the PR027 tetraploid rice two-line restoring line (male parent).

As shown in FIG. 2, FIG. 2 is the picture of real products of the tetraploid two-line hybrid rice PH083 and parents thereof of the present embodiment, wherein the left is the PS002 tetraploid rice two-line sterile line (female parent); the middle is the tetraploid two-line hybrid rice PH083; and the right is the PR027 tetraploid rice two-line restoring line (male parent). It can be seen from the figure: compared with the parents, hybrid PH083 has better growth vigour and more tillering, and the ear length, grain number per ear and thousand seed weight are all prior to those of the parents, indicating that the tetraploid two-line hybrid rice has strong heterosis.

Embodiment 3 the Breeding Process of the Tetraploid Two-Line Hybrid Rice PH107

(a) Determining a tetraploid rice photo (thermo) sensitive genic male sterile line with the gene characteristic of PMeS and a tetraploid rice two-line restoring line with the gene characteristic of PMeS; and adopting the tetraploid rice genic male sterile line PS003 containing PMeS genes as the sterile line for preparing a two-line tetraploid hybrid combination and the tetraploid rice two-line restoring line PR076 containing PMeS genes as the restoring line of the tetraploid two-line hybrid rice;

(b) determining that the hybrid combination manner of indica sterile/*japonica* restoring is used for hybridizing and matching the indica sterile line PS003 and the *japonica* restoring line PR076;

(c) performing heterosis detection on the PS003 tetraploid rice two-line sterile line in the aspects of growth period, morphological characters, flowering habit, sterile and transformation characteristics, heterogamety and preparation combination;

(d) performing heterosis detection analysis on the PR076 tetraploid two-line restoring line in the aspects of growth period, morphological characteristics, flowering habit, anther characteristics, heterogamety and preparation combination;

(e) preparing tetraploid rice hybrids by adopting the PS003 tetraploid rice two-line sterile line and the PR076 two-line restoring line;

(f) performing line comparison on the prepared tetraploid rice hybrid, and comparing with the tetraploid rice restoring line and control diploid hybrid from the aspects of growth period, morphological characteristics, resistance and flowering habit and setting percentage;

(g) breeding the combination hybrid of PS003×PR076, which is specifically shown as a uniform stable tetraploid combination hybrid with excellent morphological characteristics, appropriate growth period (sown in appropriate reason in Wuhan, with the total growth period of 134-136 days), relatively strong resistance, setting percentages of more than 84%, and yield increase of more than 4.8% than the tetraploid rice restoring lines and the control diploid hybrid, and determining as the tetraploid two-line hybrid rice, named as PH107.

Figure 3:
FIG. 3 is the picture of real products of the tetraploid two-line hybrid rice PH107 and parents thereof of embodiment 3, wherein the left is the PS003 tetraploid rice two-line sterile line (female parent); the middle is the tetraploid two-line hybrid rice PH107; and the right is the PR076 tetraploid rice two-line restoring line (male parent).

As shown in FIG. 3, FIG. 3 is the picture of real products of the tetraploid two-line hybrid rice PH107 and parents thereof of present embodiment, wherein the left is the PS003 tetraploid rice two-line sterile line (female parent); the middle is the tetraploid two-line hybrid rice PH107; and the right is the PR076 tetraploid rice two-line restoring line (male parent). It can be seen from the figure: compared with the parents, hybrid PH107 has better growth vigour and more tillering, and the ear length, grain number ear and setting percentage are all prior to those of the parents, indicating that the tetraploid two-line hybrid rice has strong heterosis.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments are chosen and described in order to explain the principles of the disclosure and their practical application so as to activate others skilled in the art to utilize the disclosure and various embodiments and with various modifications as are suited to the particular use contemplated. Alternative embodiments will become apparent to those skilled in the art to which the present disclosure pertains without departing from its spirit and scope. Accordingly, the scope of the present disclosure is defined by the appended claims rather than the foregoing description and the exemplary embodiments described therein.

What is claimed is:

1. A breeding method for producing a polyploid two-line hybrid rice, comprising:
   (a) providing the tetraploid rice photo thermosensitive genic male sterile line PS001 having polyploid meiosis stability (PMeS) gene and the tetraploid rice two-line restoring line PR005 having the PMeS gene, wherein PS001 is an indica sterile line, sample of seed of said line is deposited under CCTCC No: P202008; and wherein PR005 is a *japonica* restoring line, sample of seed of said line is deposited under CCTCC No: P202009;
   (b) hybridizing plants of the tetraploid rice photo thermosensitive genic male sterile line PS001 with plants of the tetraploid rice two-line restoring line to obtain tetraploid two-line rice hybrid seed;
   (c) growing the tetraploid two-line rice hybrid seed to produce tetraploid two-line rice hybrid plants; and
   (d) selecting one or more of the tetraploid rice hybrid plants having a setting percentage of over 80%, and a yield increase of more than 4% than that of the tetraploid rice two-line restoring line PR005 and the control diploid hybrid rice plant of line Fengliangyou No: 4, wherein the selected one or more tetraploid rice hybrid plants are determined as tetraploid two-line hybrid rice plants.

2. A tetraploid two-line hybrid rice plant, 2n=4X=48, obtained by the breeding method according to claim 1, wherein the plant has a setting percentage of more than 80%, and is named as PH015, a representative sample of seed of said plant is deposited under CCTCC No: P202005.

* * * * *